US008640704B2

(12) United States Patent
Spoo et al.

(10) Patent No.: US 8,640,704 B2

(45) Date of Patent: Feb. 4, 2014

(54) FLAT-FOLD FILTERING FACE-PIECE RESPIRATOR HAVING STRUCTURAL WELD PATTERN

(75) Inventors: Scott A. Spoo, Deer Park, WI (US); Dean R. Duffy, Woodbury, MN (US); Nhat Ha Nguyen, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1157 days.

(21) Appl. No.: 12/562,239

(22) Filed: Sep. 18, 2009

(65) Prior Publication Data

US 2011/0067700 A1 Mar. 24, 2011

(51) Int. Cl.

*A62B 7/10* (2006.01)
*A62B 18/02* (2006.01)
*A62B 23/02* (2006.01)
*A61B 19/00* (2006.01)

(52) U.S. Cl.

USPC ...................................... 128/206.19; 128/863

(58) Field of Classification Search

USPC ............. 128/205.29, 206.12–206.19, 206.28, 128/207.11, 200.24, 201.17, 201.22, 128/201.23, 201.25, 846, 857, 863; 433/73, 433/93, 136–138, 140, 229

See application file for complete search history.

(56) References Cited

U.S. PATENT DOCUMENTS

D249,072 S 8/1978 Revoir
4,417,575 A 11/1983 Hilton et al.
4,419,994 A 12/1983 Hilton
4,536,440 A 8/1985 Berg
D285,374 S 8/1986 Huber et al.
4,606,341 A 8/1986 Hubbard et al.
4,807,619 A 2/1989 Dyrud et al.
4,850,347 A 7/1989 Skov
5,524,641 A * 6/1996 Battaglia ........................ 128/846
5,701,893 A 12/1997 Kern et al.
6,041,782 A 3/2000 Angadjivand et al.
6,173,712 B1 1/2001 Brunson
D443,927 S 6/2001 Chen (Continued)

FOREIGN PATENT DOCUMENTS

EP 0756881 A2 2/1997
WO WO 2006/019472 A1 2/2006

OTHER PUBLICATIONS

Guangzhou Weini K810C Mask product literature obtained from internet on May 4, 2010 (http://www.n95.cn/K810C.html).
European Application 10177255 Search Report dated Dec. 17, 2010.

*Primary Examiner* — Jackie Ho
*Assistant Examiner* — Mark K Han
(74) *Attorney, Agent, or Firm* — Karl G. Hanson

(57) ABSTRACT

A flat-fold filtering face piece respirator 10 that comprises a mask body 12 that has a transversely-extending line of demarcation 22 and a longitudinal axis 34. First and second weld patterns 32*a*, 32*b* are disposed above and not traversing the line of demarcation on each side of the longitudinal axis 34, respectively. Third and fourth weld patterns 32*c*, 32*d* are disposed below and not crossing the line of demarcation 22 on each side of the longitudinal axis 34, respectively. Each of the first, second, third, and fourth weld patterns 32*a*-32*d* is a two-dimensional enclosed pattern. This combined weld patterns can provide a mask body that exhibits crush resistance without the need for additional or heavier layers, which may cause higher pressure drops across the filtering structure.

17 Claims, 3 Drawing Sheets

(56) References Cited

U.S. PATENT DOCUMENTS

| | | | | |
|---|---|---|---|---|
| D448,472 | S | 9/2001 | Chen | |
| 6,336,459 | B1 | 1/2002 | Miyake et al. | |
| 6,394,090 | B1 * | 5/2002 | Chen et al. | 128/206.12 |
| D459,471 | S | 6/2002 | Curran et al. | |
| D460,247 | S | 7/2002 | Liu et al. | |
| 6,484,722 | B2 | 11/2002 | Bostock et al. | |
| 6,568,392 | B1 | 5/2003 | Bostock et al. | |
| 6,923,182 | B2 | 8/2005 | Angadjivand | |
| 7,131,442 | B1 | 11/2006 | Kronzer et al. | |
| 7,145,054 | B2 * | 12/2006 | Zander et al. | 604/380 |
| 7,677,248 | B2 * | 3/2010 | Gerson et al. | 128/206.19 |
| 8,528,560 | B2 * | 9/2013 | Duffy | 128/206.19 |
| 2004/0255946 | A1 | 12/2004 | Gerson et al. | |
| 2006/0130841 | A1 | 6/2006 | Spence et al. | |
| 2009/0078261 | A1 | 3/2009 | Martin et al. | |
| 2012/0000473 | A1 * | 1/2012 | Shigematsu et al. | 128/863 |

* cited by examiner

FLAT-FOLD FILTERING FACE-PIECE RESPIRATOR HAVING STRUCTURAL WELD PATTERN

The present invention pertains to a flat-fold filtering face-piece respirator that has a weld pattern disposed on its front surface, which weld pattern assists in providing a collapse resistant structure to the mask body.

BACKGROUND

Respirators are commonly worn over the breathing passages of a person for at least one of two common purposes: (1) to prevent impurities or contaminants from entering the wearer's breathing track; and (2) to protect other persons or things from being exposed to pathogens and other contaminants exhaled by the wearer. In the first situation, the respirator is worn in an environment where the air contains particles that are harmful to the wearer, for example, in an auto body shop. In the second situation, the respirator is worn in an environment where there is risk of contamination to other persons or things, for example, in an operating room or a clean room.

A variety of respirators have been designed to meet either (or both) of these purposes. Some respirators have been categorized as being "filtering face-pieces" because the mask body itself functions as the filtering mechanism. Unlike respirators that use rubber or elastomeric mask bodies in conjunction with attachable filter cartridges (see, e.g., U.S. Pat. RE39,493 to Yuschak et al.) or insert-molded filter elements (see, e.g., U.S. Pat. No. 4,790,306 to Braun), filtering face-piece respirators are designed to have the filter media cover much of the whole mask body so that there is no need for installing or replacing a filter cartridge. Filtering face-piece respirators commonly come in one of two configurations: molded respirators and flat-fold respirators.

Molded filtering face piece respirators have regularly comprised non-woven webs of thermally-bonded fibers or open-work plastic meshes to furnish the mask body with its cup-shaped configuration. Molded respirators tend to maintain the same shape during both use and storage. Examples of patents that disclose molded, filtering, face-piece respirators include U.S. Pat. No. 7,131,442 to Kronzer et al, U.S. Pat Nos. 6,923,182, 6,041,782 to Angadjivand et al., U.S. Pat No. 4,850,347 to Skov, U.S. Pat. No. 4,807,619 to Dyrud et al., U.S. Pat No. 4,536,440 to Berg, and Des. 285,374 to Huber et al. Flat-fold respirators—as their name implies—can be folded flat for shipping and storage. Examples of flat-fold respirators are shown in U.S. Pat. Nos. 6,568,392 and 6,484,722 to Bostock et al. and in U.S. Pat. No. 6,394,090 to Chen.

During use, filtering face-piece respirators should maintain their intended cup-shaped configuration. After being worn numerous times and being subjected to high quantities of moisture from a wearer's exhalations, in conjunction with having the mask bump into other objects while being worn on a person's face, known masks can be susceptible to collapsing or having an indentation pressed into the shell. The wearer can remove this indentation by displacing the mask from their face and pressing on the indentation from the mask interior. To preclude masks from collapsing during use, additional layers have been added to the mask body structure to improve its structural integrity. U.S. Pat. No. 6,923,182 to Angadjivand et al., for example, uses first and second adhesive layers between the filtration layer and first and second shaping layers to provide a crush-resistant molded filtering face mask. To preserve the structural integrity of a flat-fold respirator, U.S. Pat. No. 6,394,090 to Chen provides first and second lines of demarcation on the mask body to assist in preventing collapse during use.

SUMMARY OF THE INVENTION

The present invention provides a new flat-fold filtering face-piece respirator construction that assists in preventing mask body collapse during use. The respirator of the present invention comprises a mask body and a harness. The mask body has a transversely-extending line of demarcation, a longitudinal axis and first and second weld patterns disposed above and not traversing the line of demarcation on each side of the longitudinal axis, respectively. Third and forth weld patterns are disposed below and not crossing the line of demarcation on each side of the longitudinal axis, respectively. Each of the first, second, third, and fourth weld patterns is a two-dimensional enclosed pattern.

The present invention is directed to providing a flat-fold filtering face-piece respirator that possesses crush resistant properties that minimize mask shape deformation caused by extended use or rough handling. The respirator also is less likely to lose its structural integrity from particle loading and/or moisture build-up. Because the filtering face-piece respirator is less likely to collapse during use, it therefore presents the benefit of improving wearer comfort and convenience. Further, there is less need for additional layers or heavier layers to provide collapse resistant qualities. The use of additional layers can result in increased breathing resistance and product cost. The present invention therefore presents the benefit of preserving the intended in-use shape of the mask body in conjunction with improving wearer comfort without the added cost of additional or heavier layers.

GLOSSARY

The terms set forth below will have the meanings as defined:

"bisect(s)" means to divide into two generally equal parts;

"comprises (or comprising)" means its definition as is standard in patent terminology, being an open-ended term that is generally synonymous with "includes", "having", or "containing". Although "comprises", "includes", "having", and "containing" and variations thereof are commonly-used, open-ended terms, this invention also may be suitably described using narrower terms such as "consists essentially of", which is a semi open-ended term in that it excludes only those things or elements that would have a deleterious effect on the performance of the inventive respirator in serving its intended function;

"clean air" means a volume of atmospheric ambient air that has been filtered to remove contaminants;

"contaminants" means particles (including dusts, mists, and fumes) and/or other substances that generally may not be considered to be particles (e.g., organic vapors, et cetera) but which may be suspended in air;

"crosswise dimension" is the dimension that extends laterally across the respirator from side-to-side when the respirator is viewed from the front;

"cup-shaped configuration" means any vessel-type shape that is capable of adequately covering the nose and mouth of a person;

"exterior gas space" means the ambient atmospheric gas space into which exhaled gas enters after passing through and beyond the mask body and/or exhalation valve;

"filtering face-piece" means that the mask body itself is designed to filter air that passes through it; there are no separately identifiable filter cartridges or insert-molded filter elements attached to or molded into the mask body to achieve this purpose;

"filter" or "filtration layer" means one or more layers of air-permeable material, which layer(s) is adapted for the primary purpose of removing contaminants (such as particles) from an air stream that passes through it;

"filter media" means an air-permeable structure that is designed to remove contaminants from air that passes through it;

"filtering structure" means a construction that includes a filter media or a filtration layer;

"first side" means an area of the mask body that is located on one side of a plane that bisects the mask body normal to the cross-wise dimension;

"fitment" means any one or combination of donning, doffing, or the adjusting mask body;

"flange" means a protruding part that has sufficient surface area to be grasped by a person;

"frontally" means extending away from the mask body perimeter when the mask body is in a folded condition;

"harness" means a structure or combination of parts that assists in supporting the mask body on a wearer's face;

"indicia" means an identifying mark(s), pattern(s), image (s), opening(s), or combination thereof;

"integral" means being manufactured together at the same time; that is, being made together as one part and not two separately manufactured parts that are subsequently joined together;

"interior gas space" means the space between a mask body and a person's face;

"laterally" means extending away from a plane that bisects the mask body normal to the cross-wise dimension when the mask body is in a folded condition;

"line of demarcation" means a fold, seam, weld line, bond line, stitch line, hinge line, and/or any combination thereof;

"longitudinal axis" means a line that bisects the mask body normal to the cross-wise dimension;

"mask body" means an air-permeable structure that is designed to fit over the nose and mouth of a person and that helps define an interior gas space separated from an exterior gas space (including the seams and bonds that join layers and parts thereof together);

"nose clip" means a mechanical device (other than a nose foam), which device is adapted for use on a mask body to improve the seal at least around a wearer's nose;

"perimeter" means the outer edge of the mask body, which outer edge would be disposed generally proximate to a wearer's face when the respirator is being donned by a person;

"pleat" means a portion that is designed to be or is folded back upon itself;

"polymeric" and "plastic" each mean a material that mainly includes one or more polymers and that may contain other ingredients as well;

"plurality" means two or more;

"respirator" means an air filtration device that is worn by a person to provide the wearer with clean air to breathe;

"second side" means an area of the mask body that is located on one side of a plane that bisects the mask body normal to the cross-wise dimension (the second side being opposite the first side);

"snug fit" or "fit snugly" means that an essentially air-tight (or substantially leak-free) fit is provided (between the mask body and the wearer's face);

"tab" means a part that exhibits sufficient surface area for attachment of another component; and "transversely extending" means extending generally in the crosswise dimension.

DETAILED DESCRIPTION OF PREFERRED EMBODIMENTS

In practicing the present invention, a flat-fold, filtering face-piece respirator is provided that has a weld pattern disposed on the mask body to help improve collapse resistance.

Figure 1:
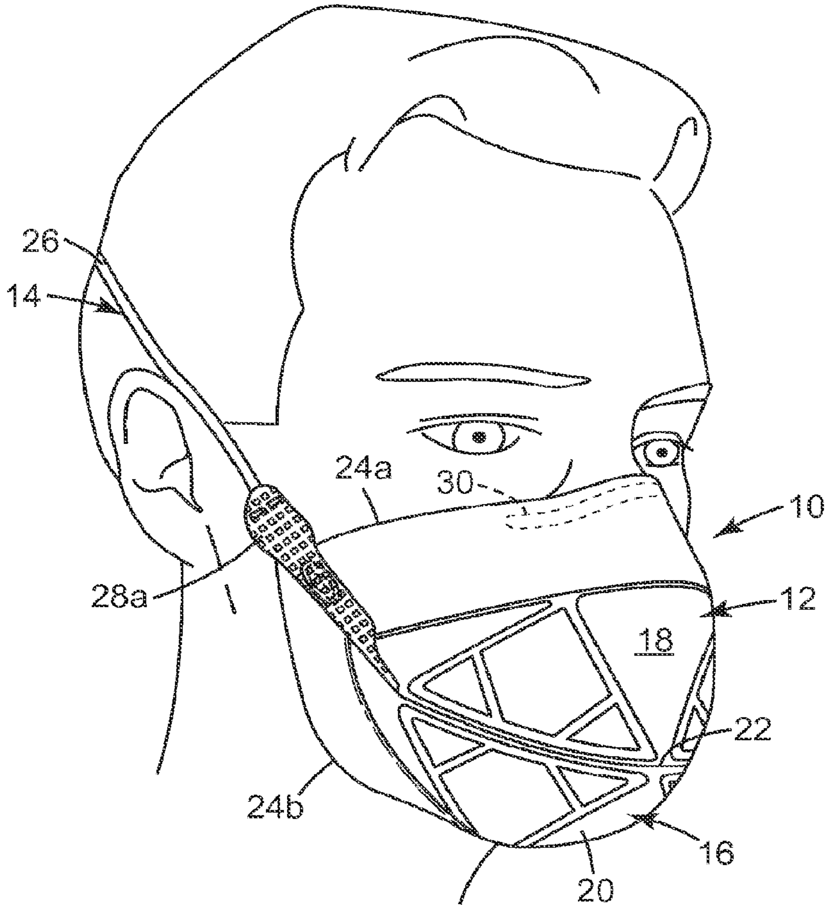
FIG. 1 is a perspective view of a flat-fold filtering face-piece respirator 10 in accordance with the present invention.

FIG. 1 shows an example of a flat-fold filtering face-piece respirator 10 in an opened condition on the face of a wearer. The respirator 10 may be used in accordance with the present invention to provide clean air for the wearer to breathe. As illustrated, the filtering face-piece respirator 10 includes a mask body 12 and a harness 14. The mask body 12 has a filtering structure 16 through which inhaled air must pass before entering the wearer's respiratory system. The filtering structure 16 removes contaminants from the ambient environment so that the wearer breathes clean air. The mask body 12 includes a top portion 18 and a bottom portion 20. The top portion 18 and the bottom portion 20 are separated by a line of demarcation 22. In this particular embodiment, the line of demarcation 22 is a pleat that extends transversely across the central portion of the mask body. The mask body 12 also includes a perimeter that includes an upper segment 24*a* and a lower segment 24*b*. The harness 14 has a strap 26 that is stapled to a tab 28*a*. A nose clip 30 may be placed on the mask body 12 on the top portion 18 of the mask body 12 on its outer surface or beneath a cover web.

Figure 2:
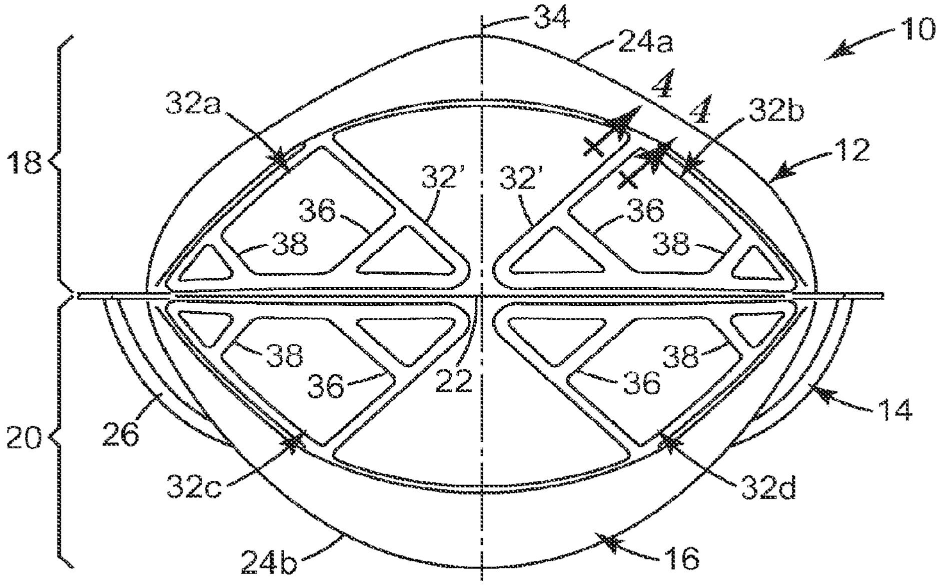
FIG. 2 is a front view of the flat-fold filtering face-piece respirator 10 shown in FIG. 1.

FIG. 2 illustrates that the flat-fold respirator 10 has first and second weld patterns 32*a*, 32*b*, disposed above and not traversing the line of demarcation 22. The first and second weld patterns 32*a*, 32*b* are located on each side of the longitudinal axis 34. The third and fourth weld patterns 32*c* and 32*d* are disposed below and not crossing the line of demarcation 22. The weld patterns 32*c* and 32*d* also are located on each side of the longitudinal axis 34. Each of the first, second, third, and fourth weld patterns 32*a*, 32*b*, 32*c*, 32*d* contains weld lines 32' that define a two-dimensional enclosed pattern. Each weld pattern may exhibit a truss-type geometry that includes, for example, a larger triangle that has rounded corners and that has a pair of triangles 36 and 38 located within it. Each of the triangles 36, 38 is nested within the larger triangle 32*a*-32*d* such that the two sides of each of the triangles 36, 38 also forms a partial side of each of the triangles 32*a*-32*d*. The rounded corners typically have a minimum radius of about 0.5 millimeters (mm) As shown in FIG. 2, the weld patterns 32*a*-32*d* are provided on the mask body 12 such that there is symmetry on each side of the longitudinal axis 34 or on each side of the line of demarcation 22 and the longitudinal axis 34. Although the invention has been illustrated in the present drawings as being triangular patterns within a triangle, the two-dimensional enclosed patterns may take on other truss-type forms, including quadrilaterals that are, rectangular, trapezoidal, rhombusal, etc., which are welded into the mask body. Each two-dimensional enclosed weld pattern may occupy a surface area of about 5 to 30 square centimeters ($cm^2$), more commonly about 10 to 16 $cm^2$.

Figure 3:
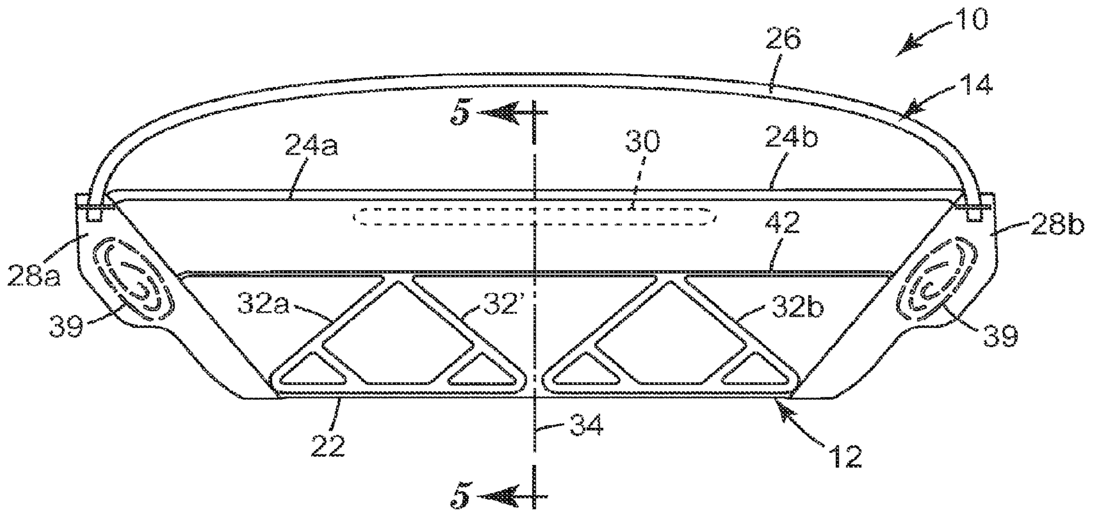
FIG. 3 is a top view of the filtering face-piece respirator 10 of FIG. 1 in a folded condition.

FIG. 3 shows the mask body 12 in a horizontally folded condition, which condition is particularly beneficial for shipping and off-the-face storage. The mask body 12 can be folded along the horizontal line of demarcation 22. The respirator may include one or more straps 26 that are attached to first and second tabs 28*a*, 28*b*, and indicia 39 may be placed on each tab 28*a*, 28*b* to provide an indication of where the wearer may grasp the mask body for donning, doffing, and adjusting fit. The indicia 39 that may be provided on each of the flanges is further described in copending patent application entitled Filtering Face Piece Respirator Having Grasping Feature Indicator, attorney case number 65657US002, filed on the same day as this patent application.

Figure 4:
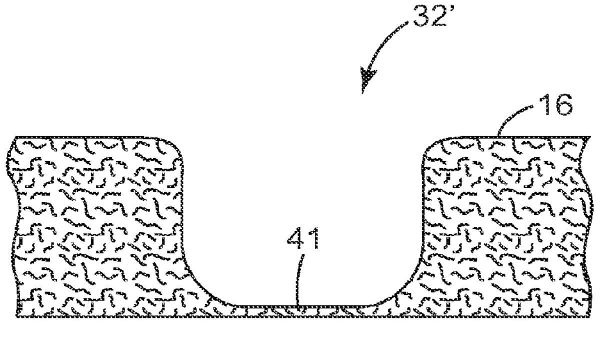
FIG. 4 is an enlarged cross-section of a weld line 32' in a weld pattern 32*b*, taken along lines 4-4 of FIG. 2.

FIG. 4 shows a cross-section of a weld line 32' in the weld pattern 32*b*. The weld lines in the weld patterns 32*a*, 32*c*, and 32*d* may have a similar cross-sectional configuration. The weld line 32' compresses the fibers in the filtering structure such that they become mostly solidified into a nonporous solid-type bond. The weld line 32' may be about 2 to 7 mm wide, more commonly about 4 to 5 mm wide. If the filtering structure 16 comprises more than one layer, these layers essentially become merged together at the base 41 of the weld line 32'.

Figure 5:
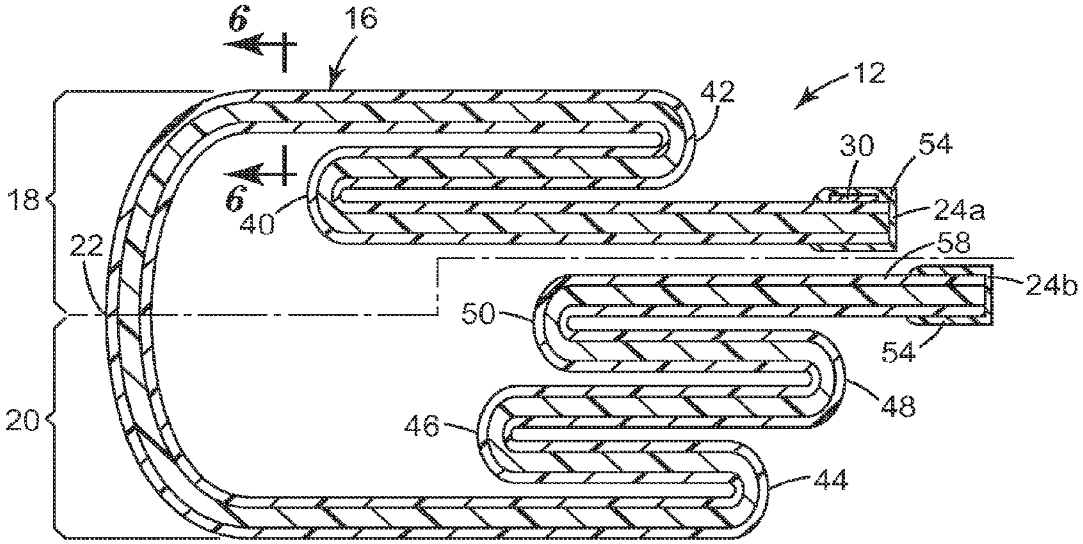
FIG. 5 is a cross-section of the respirator mask body 12 taken along lines 5-5 of FIG. 3.

FIG. 5 illustrates an example of a pleated configuration for a mask body 12 in accordance with the present invention. As shown, the mask body 12 includes pleat 22 already described with reference to FIGS. 1-3. The upper portion or panel 18 of the mask body 12 also includes pleats 40 and 42. The lower portion or panel 20 of the mask body 12 includes pleats 44, 46, 48, and 50. The lower portion 20 of the mask body 12 may include more filter media surface area than the upper portion 18. The mask body 12 also includes a perimeter web 54 that is secured to the mask body along its perimeter. The perimeter web 54 may be folded over the mask body at the perimeter 24*a*, 24*b*. The perimeter web 54 also may be an extension of the inner cover web 58 folded and secured around the edge of 24*a* and 24*b*. The nose clip 30 may be disposed on the upper portion 18 of the mask body centrally adjacent to the perimeter 24*a* between the filtering structure 16 and the perimeter web 54. The nose clip 30 may be made from a pliable dead soft metal or plastic that is capable of being manually adapted by the wearer to fit the contour of the wearer's nose. The nose clip may be made from aluminum and may be linear as shown in FIG. 3, or it may take on other shapes when viewed from the top such as the m-shaped nose clip shown in U.S. Pat. No. 5,558,089 and Des. 412,573 to Castiglione.

Figure 6:
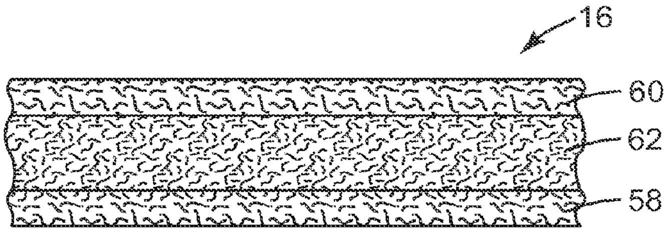
FIG. 6 is a cross-section of the filtering structure 16 taken along lines 6-6 of FIG. 5.

FIG. 6 illustrates that the filtering structure 16 may include one or more layers such as an inner cover web 58, an outer cover web 60, and a filtration layer 62. The inner and outer cover webs 58 and 60 may be provided to protect the filtration layer 62 and to preclude fibers from the filtration layer 62 from coming loose and entering the mask interior. During respirator use, air passes sequentially through layers 60, 62, and 58 before entering the mask interior. The air that is disposed within the interior gas space of the mask may then be inhaled by the wearer. When a wearer exhales, the air passes in the opposite direction sequentially through layers 58, 62, and 60. Alternatively, an exhalation valve (not shown) may be provided on the mask body to allow exhaled air to be rapidly purged from the interior gas space to enter the exterior gas space without passing through filtering structure 16. Typically, the cover webs 58 and 60 are made from a selection of nonwoven materials that provide a comfortable feel, particularly on the side of the filtering structure that makes contact with the wearer's face. The construction of various filter layers and cover webs that may be used in conjunction with the support structure of the present invention are described below in more detail. To improve wearer fit and comfort, an elastomeric face seal can be secured to the perimeter of the filtering structure 16. Such a face seal may extend radially inward to contact the wearer's face when the respirator is being donned. Examples of face seals are described in U.S. Pat. No. 6,568,392 to Bostock et al., U.S. Pat No. 5,617,849 to Springett et al., and , U.S. Pat No. 4,600,002 to Maryyanek et al., and in Canadian Patent 1,296,487 to Yard. The filtering structure also may have a structural netting or mesh juxtaposed against at least one or more of the layers 58, 60, or 62, typically against the outer surface of the outer cover web 60. The use of such a mesh is described in U.S. patent application Ser. No. 12/338,091, filed Dec. 18, 2008, entitled Expandable Face Mask with Reinforcing Netting.

The mask body that is used in connection with the present invention may take on a variety of different shapes and configurations. Generally the shape and configuration of the filtering structure corresponds to the general shape of the mask body. Although a filtering structure has been illustrated with multiple layers that include a filtration layer and two cover webs, the filtering structure may simply comprise a filtration layer or a combination of filtration layers. For example, a pre-filter may be disposed upstream to a more refined and selective downstream filtration layer. Additionally, sorptive materials such as activated carbon may be disposed between the fibers and/or various layers that comprise the filtering structure. Further, separate particulate filtration layers may be used in conjunction with sorptive layers to provide filtration for both particulates and vapors. The filtering structure may include one or more stiffening layers that assist in providing a cup-shaped configuration. The filtering structure also could have one or more horizontal and/or vertical lines of demarcation that contribute to its structural integrity. Using the first and second flanges in accordance with the present invention, however, may make unnecessary the need for such stiffening layers and lines of demarcation.

The filtering structure that is used in a mask body of the invention can be of a particle capture or gas and vapor type filter. The filtering structure also may be a barrier layer that prevents the transfer of liquid from one side of the filter layer to another to prevent, for instance, liquid aerosols or liquid splashes (e.g. blood) from penetrating the filter layer. Multiple layers of similar or dissimilar filter media may be used to construct the filtering structure of the invention as the application requires. Filters that may be beneficially employed in a layered mask body of the invention are generally low in pressure drop (for example, less than about 195 to 295 Pascals at a face velocity of 13.8 centimeters per second) to minimize the breathing work of the mask wearer. Filtration layers additionally are flexible and have sufficient shear strength so that they generally retain their structure under the expected use conditions. Examples of particle capture filters include one or more webs of fine inorganic fibers (such as fiberglass) or polymeric synthetic fibers. Synthetic fiber webs may include electret-charged polymeric microfibers that are produced from processes such as meltblowing. Polyolefin microfibers formed from polypropylene that has been electrically charged provide particular utility for particulate capture applications. An alternate filter layer may comprise a sorbent component for removing hazardous or odorous gases from the breathing air. Sorbents may include powders or granules that are bound in a filter layer by adhesives, binders, or fibrous structures—see U.S. Pat. No. 6,334,671 to Springett et al. and, U.S. Pat No. 3,971,373 to Braun. A sorbent layer can be formed by coating a substrate, such as fibrous or reticulated foam, to form a thin coherent layer. Sorbent materials may include activated carbons that are chemically treated or not, porous alumna-silica catalyst substrates, and alumna particles. An example of a sorptive filtration structure that may be conformed into various configurations is described in U.S. Pat. No. 6,391,429 to Senkus et al.

The filtration layer is typically chosen to achieve a desired filtering effect. The filtration layer generally will remove a high percentage of particles and/or or other contaminants from the gaseous stream that passes through it. For fibrous filter layers, the fibers selected depend upon the kind of substance to be filtered and, typically, are chosen so that they do not become bonded together during the molding operation. As indicated, the filtration layer may come in a variety of shapes and forms and typically has a thickness of about 0.2 millimeters (mm) to 1 centimeter (cm), more typically about 0.3 mm to 0.5 cm, and it could be a generally planar web or it could be corrugated to provide an expanded surface area—see, for example, U.S. Pat. Nos. 5,804,295 and 5,656,368 to Braun et al. The filtration layer also may include multiple filtration layers joined together by an adhesive or any other means. Essentially any suitable material that is known (or later developed) for forming a filtering layer may be used as the filtering material. Webs of melt-blown fibers, such as those taught in Wente, Van A., *Superfine Thermoplastic Fibers,* 48 Indus. Engn. Chem., 1342 et seq. (1956), especially when in a persistent electrically charged (electret) form are especially useful (see, for example, U.S. Pat. No. 4,215, 682 to Kubik et al.). These melt-blown fibers may be microfibers that have an effective fiber diameter less than about 20 micrometers (μm) (referred to as BMF for "blown microfiber"), typically about 1 to 12 μm. Effective fiber diameter may be determined according to Davies, C. N., *The Separation Of Airborne Dust Particles*, Institution Of Mechanical Engineers, London, Proceedings 1B, 1952. Particularly preferred are BMF webs that contain fibers formed from polypropylene, poly(4-methyl-1-pentene), and combinations thereof. Electrically charged fibrillated-film fibers as taught in van Turnhout, U.S. Pat. Re. 31,285, also may be suitable, as well as rosin-wool fibrous webs and webs of glass fibers or solution-blown, or electrostatically sprayed fibers, especially in microfilm form. Electric charge can be imparted to the fibers by contacting the fibers with water as disclosed in U.S. Pat. No. 6,824,718 to Eitzman et al., U.S. Pat No. 6,783,574 to Angadjivand et al., U.S. Pat No. 6,743,464 to Insley et al., , U.S. Pat Nos. 6,454,986 and 6,406,657 to Eitzman et al., and U.S. Pat No. 6,375,886 and 5,496,507 to Angadjivand et al. Electric charge also may be imparted to the fibers by corona charging as disclosed in U.S. Pat. No. 4,588,537 to Klasse et al. or by tribocharging as disclosed in U.S. Pat. No. 4,798,850 to Brown. Also, additives can be included in the fibers to enhance the filtration performance of webs produced through the hydro-charging process (see U.S. Pat. No. 5,908,598 to Rousseau et al.). Fluorine atoms, in particular, can be disposed at the surface of the fibers in the filter layer to improve filtration performance in an oily mist environment—see U.S. Pat. No. 6,398,847 B, U.S. Pat No. 1, 6,397,458 B1, and , U.S. Pat No. 6,409,806 B1 to Jones et al. Typical basis weights for electret BMF filtration layers are about 10 to 100 grams per square meter. When electrically charged according to techniques described in, for example, the '507 Angadjivand et al. patent, and when including fluorine atoms as mentioned in the Jones et al. patents, the basis weight may be about 20 to 40 $g/m^2$ and about 10 to 30 $g/m^2$, respectively.

An inner cover web can be used to provide a smooth surface for contacting the wearer's face, and an outer cover web can be used to entrap loose fibers in the mask body or for aesthetic reasons. The cover web typically does not provide any substantial filtering benefits to the filtering structure, although it can act as a pre-filter when disposed on the exterior (or upstream to) the filtration layer. To obtain a suitable degree of comfort, an inner cover web preferably has a comparatively low basis weight and is formed from comparatively fine fibers. More particularly, the cover web may be fashioned to have a basis weight of about 5 to 50 $g/m^2$ (typically 10 to 30 $g/m^2$), and the fibers may be less than 3.5 denier (typically less than 2 denier, and more typically less than 1 denier but greater than 0.1). Fibers used in the cover web often have an average fiber diameter of about 5 to 24 micrometers, typically of about 7 to 18 micrometers, and more typically of about 8 to 12 micrometers. The cover web material may have a degree of elasticity (typically, but not necessarily, 100 to 200% at break) and may be plastically deformable.

Suitable materials for the cover web may be blown microfiber (BMF) materials, particularly polyolefin BMF materials, for example polypropylene BMF materials (including polypropylene blends and also blends of polypropylene and polyethylene). A suitable process for producing BMF materials for a cover web is described in U.S. Pat. No. 4,013,816 to Sabee et al. The web may be formed by collecting the fibers on a smooth surface, typically a smooth-surfaced drum or a rotating collector—see U.S. Pat. No. 6,492,286 to Berrigan et al. Spun-bond fibers also may be used.

A typical cover web may be made from polypropylene or a polypropylene/polyolefin blend that contains 50 weight percent or more polypropylene. These materials have been found to offer high degrees of softness and comfort to the wearer and also, when the filter material is a polypropylene BMF material, to remain secured to the filter material without requiring an adhesive between the layers. Polyolefin materials that are suitable for use in a cover web may include, for example, a single polypropylene, blends of two polypropylenes, and blends of polypropylene and polyethylene, blends of polypropylene and poly(4-methyl-1-pentene), and/or blends of polypropylene and polybutylene. One example of a fiber for the cover web is a polypropylene BMF made from the polypropylene resin "Escorene 3505G" from Exxon Corporation, providing a basis weight of about 25 $g/m^2$ and having a fiber denier in the range 0.2 to 3.1 (with an average, measured over 100 fibers of about 0.8). Another suitable fiber is a polypropylene/polyethylene BMF (produced from a mixture comprising 85 percent of the resin "Escorene 3505G" and 15 percent of the ethylene/alpha-olefin copolymer "Exact 4023" also from Exxon Corporation) providing a basis weight of about 25 $g/m^2$ and having an average fiber denier of about 0.8. Suitable spunbond materials are available, under the trade designations "Corosoft Plus 20", "Corosoft Classic 20" and "Corovin PP-S-14", from Corovin GmbH of Peine, Germany, and a carded polypropylene/viscose material available, under the trade designation "370/15", from J. W. Suominen OY of Nakila, Finland.

Cover webs that are used in the invention preferably have very few fibers protruding from the web surface after processing and therefore have a smooth outer surface. Examples of cover webs that may be used in the present invention are disclosed, for example, in U.S. Pat. No. 6,041,782 to Angadjivand, U.S. Pat. No. 6,123,077 to Bostock et al., and WO 96/28216A to Bostock et al.

The strap(s) that are used in the harness may be made from a variety of materials, such as thermoset rubbers, thermoplastic elastomers, braided or knitted yarn/rubber combinations, inelastic braided components, and the like. The strap(s) may be made from an elastic material such as an elastic braided material. The strap preferably can be expanded to greater than twice its total length and be returned to its relaxed state. The strap also could possibly be increased to three or four times its relaxed state length and can be returned to its original condition without any damage thereto when the tensile forces are removed. The elastic limit thus is preferably not less than two, three, or four times the length of the strap when in its relaxed state. Typically, the strap(s) are about 20 to 30 cm long, 3 to 10 mm wide, and about 0.9 to 1.5 mm thick. The strap(s) may extend from the first tab to the second tab as a continuous strap or the strap may have a plurality of parts, which can be joined together by further fasteners or buckles. For example, the strap may have first and second parts that are joined together by a fastener that can be quickly uncoupled by the wearer when removing the mask body from the face. An example of a strap that may be used in connection with the present invention is shown in U.S. Pat. No. 6,332,465 to Xue et al. Examples of fastening or clasping mechanism that may be used to joint one or more parts of the strap together is shown, for example, in the following U.S. Pat. No. 6,062,221 to Brostrom et al., U.S. Pat No. 5,237,986 to Seppala, and EP1, 495,785A1 to Chien.

As indicated, an exhalation valve may be attached to the mask body to facilitate purging exhaled air from the interior gas space. The use of an exhalation valve may improve wearer comfort by rapidly removing the warm moist exhaled air from the mask interior. See, for example, U.S. Pat. Nos. 7,188,622, 7,028,689, and 7,013,895 to Martin et al.; U.S. Pat Nos. 7,428,903, 7,311,104, 7,117,868, 6,854,463, 6,843,248, and 5,325,892 to Japuntich et al.; , U.S. Pat No. 6,883,518 to Mittelstadt et al.; and RE37,974 to Bowers. Essentially any exhalation valve that provides a suitable pressure drop and that can be properly secured to the mask body may be used in connection with the present invention to rapidly deliver exhaled air from the interior gas space to the exterior gas space.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

EXAMPLES

General Mask Making Procedure

A respirator filtering structure was formed from three layers of nonwoven material and other respirator components. The inventive mask was assembled in two operations—preform making and mask finishing. The preform making stage included the steps of lamination and fixing of nonwoven fibrous webs, formation of pleat crease lines and attachment of perimeter web material and nose clip. The mask finishing operation included folding of pleats along embossed crease lines, fusing both the lateral mask edges and reinforced flange material, cutting the final form, and attaching a headband.

Preform Making Stage

In the preform making stage, three layers of nonwoven material were plied in face to face orientation. In the example, individual materials that formed the layers were assembled in the following order:

1. outer scrim
2. filter material
3. inner cover web

The outer scrim (indicated as 60 in FIG. 6) was a 17 grams per square meter (gsm) polypropylene spun-bonded nonwoven, available from Shandong Kangjie Nonwovens Co. Ltd., Jinan, China. The inner cover web was of the same material as the outer scrim. The filter material (indicated as 62 in FIG. 6) used in the preform was an electret-charged blown microfiber polypropylene web with a basis weight of 35 gsm, a solidity of 8% and an effective fiber size of 4.75 micrometers. The inner cover web (indicated as 58 in FIG. 6) was the same as the outer scrim. The preform was made by plying, in the desired order, layers of each material that was then cut into 20 cm by 33 cm sheets and ultrasonically welded together using a point-bonded pattern. Reinforcing weld patterns were formed into the body of the preform as desired. The weld pattern of the inventive mask was orientated relative to a transversely-extending line of demarcation and a longitudinal axis. Patterns were formed by ultrasonic welding using an ultrasonic welding unit Model 2000× from Branson, Danbury, Conn., operated at a ram pressure of 448 kPa with a horn amplitude, frequency, and dwell time of 100%, 20 kHz, and 0.5 sec, respectively. The ultrasonic horn operated against an anvil of a given pattern and with a specified contact surface area. Ultrasonic welding was done using an ultrasonic welding unit, model 2000, from Branson, Danbury, Conn., operated at a ram pressure of 483 kilo pascals (kPa) with a horn amplitude, frequency, and dwell time of 100%, 20 kHz and 0.7 sec respectively. The ultrasonic horn operated against an anvil with a field of flat-top square pegs, having individual face areas of 1.6 square millimeters, arranged in a grid pattern with spacing of approximately one centimeter on center of the pegs. The flat-faced horn of the welder acted against the anvil with a contact pressure of approximately 6 MPa. With the layers of nonwoven fixed, crease lines that define pleat location were embossed on the fixed layers of nonwoven. Embossing of the crease lines was done using a die cutting machine, Hytronic Cutting Machine Model B, from USM Corporation, Haverhill, Mass., at 15 tons of force and with a rule die. The die had nine bars with radius edges that traversed the length of the preform and when pressed into the preform created lines into the nonwoven layers. The embossed lines compressed the webs together at the point of contact and did not fuse or penetrate the material. As a final step in the preform making operation, bands of perimeter web, BBA Nonwovens, 51 grams per square meter (gsm) spun-bonded polypropylene scrim, 4 cm wide and 36 cm long were wrapped around the top and bottom edges of the preform and ultrasonically welded into place. Ultrasonic welding was carried out using an ultrasonic welding unit Model 2000× from Branson, Danbury, Conn., operated at a ram pressure of 448 kPa with a horn amplitude, frequency, and dwell time of 100%, 20 kHz, and 0.5 sec, respectively. The horn operated against an anvil with a contact surface area of 4.1 square centimeters resulted in contact pressures of 8.5 MPa to bond the materials of the preform. The area of the anvil used to bond the perimeter web material was configured in flat-top square pegs, having individual face areas of 1.6 square millimeters. The flat-faced horn of the welder acted against an anvil, fixing the perimeter web to the preform. Using this process, a nose clip was attached to the top of the preform and was encapsulated between the preform and the perimeter web. The nose clip was a malleable, plastically-deformable aluminum strip that had the shape shown in FIG. 2 and was 9 cm long by 0.5 cm wide by 1 mm thick.

Mask Finishing Operation

In the mask finishing operation, pleats were folded along crease lines as shown in FIG. 5. Pleats located above the central fold of the mask, were folded such that the exterior folds faced downwards with the mask open, this was done to help prevent accumulation of gross matter in the mask folds when worn. With the preform properly pleated and folded around the center fold, the preform was ultrasonically welded to fuse the lateral edges of the mask and to create the bonded layers of the stiffening flange (28*a* and 28*b* in FIG. 3). Ultrasonic welding was done using an ultrasonic welding unit Model 2000ae from Branson, Danbury, Conn., operated at a ram pressure of 483 kPa with a horn amplitude, frequency, and dwell time of 100%, 20 kHz, and 2.0 sec, respectively. The horn operated against the anvil with a contact surface area of 22.4 square centimeters resulted in contact pressures of 1.5 MPa to bond the materials of the preform. The contact area of the anvil for bonding the flange material was configured in flat-top square pegs, having individual face areas of 1.6 square millimeters that were spaced 1.27 millimeters apart from their flat sides, the resultant bond pattern is indicated as 28*a* in FIG. 1. The anvil bars that formed the lateral edge bonds of the mask were 95.25 millimeters long and 9.525 millimeters wide, with the resulting bond pattern as indicated on the tabs 28*a* in FIG. 1. Angled bar elements of the anvil sealed the lateral edges of the mask and pin welding surfaces fused and stiffened the flange material. As a final step in the mask finishing operation, the stiffening flanges were cut to a desired shape and a headband was stapled to the tabs. Flanges were 1.0 cm wide by 5.0 cm long with a 0.5 cm radius head located at the tab point of attachment of the headband. The headband was attached to the tabs radius head using a hand stapler from Stanley Bostitch, East Greenwich, R.I., model P6C-8 and staples No. STHSO19 ¼ inch galvanized.

Headform

Design of flat-fold respirators with the best fit and highest comfort level for a spectrum of wearers of diverse anthropometry can be augmented with the use of headforms adapted for measuring the collapse of the respirator when subjected to a simulated breathing load. This method simulated the interaction between a respirator and a headform. Head-strap forces, headform shape, mask positioning; breathing cycle volume and rate play roles in determining the collapse resistance performance of a flat-fold respirator.

The headform used in this test method was adapted with a breathing opening and contact load pad positioned on the face of the headform. Anthropometric feature dimensions of the headform are given in Table 1; these features are those outlined for characterizing head and face dimensions in respirator performance analysis described in a National Institute for Occupational Safety and Health (NIOSH) study titled "A HEAD-AND-FACE ANTHROPOMETRICSURVEY OF U.S. RESPIRATOR USERS", May 2004. A simulated breathing opening, having a 13 mm diameter round outlet on the face of the headform, was located 15.9 mm above and centered over the human analog of the Menton position—the inferior point of the mandible in the midsagittal plane (bottom of the chin). The contact load pad, with a contact activation threshold of 6.9 kPa, was in the shape of an elliptical annular ring positioned around the simulated breathing opening. The pad extended radially from the edge of the simulated breathing opening and had a thickness of 5 mm. Orientation of the contact load pad was such that the ellipse major axis was transverse to the headform, with the major axis length being 66 mm and the minor axis length being 48 mm. During testing, when contact between the mask was made with the contact load pad, a light would illuminate indicating collapse of the mask.

Masks for evaluation were fitted to the headform using two elastic bands—one that generally followed the Bitragion Subnasale Arc around to the back of the headform above the ear and a second that traversed the back of the headform under the ear. The force exerted on the mast from extending from each of four attachment points was nominally 2 Newtons (N). The mask was positioned on the headform so that the intersection of the center fold transversely-extending line of demarcation and the longitudinal axis was aligned with the center of the breathing opening. With the mask properly positioned for evaluation, the breathing cycle of the test apparatus was initiated.

TABLE 1

| Anthropometric Feature | Dimension (mm) |
|---|---|
| Bigonial Breadth | 116 |
| Bitragion Chin Arc | 375 |
| Bitragion Coronal Arc | 297 |
| Bitragion Subnasale Arc | 122 |
| Bizygomatic Breadth | 134 |
| Head Breadth | 159 |
| Head Circumference | 592 |
| Head Length | 122 |
| Interpupillary Breadth | 68 |
| Lip Length (sensor pad) | 66 |
| Maximum Frontal Breadth | 69 |
| Menton-Sellion Length | 122 |
| Nasal Root Breadth | 17 |
| Nose Breadth | 34 |
| Nose Protrusion | 27 |
| Subnasale-Sellion Length | 53 |
| Face Width | 132 |

Simulated Breathing Apparatus and Collapse Resistance Test

A Dynamic Breathing Machine, Warwick Technology Limited, Warwick, United Kingdom was used in conjunction with the previously described headform to simulate human respiration as it would be delivered to a respirator. The test apparatus was configured such that air was channeled from the breathing machine to the back of the headform through a 30 cm long 2.54 cm inner diameter hose. The breathing machine provided a breathing sine wave waveform with a flow rate, given in liters/minute (1/min) that was varied over the duration of the test. The breathing machine was operated at a respiratory frequency of 20 cycles/minute, with a tidal volume of 1 liter, and at room conditions of 25 deg C. and relative humidity of 50%.

Respirator evaluations were conducted by placing a respirator on the headform, as described in the Headform section above, and initiating the breathing apparatus at a flow rate of 20 l/min. The flow rate was then gradually increasing by increments of 5 l/min every 3 minutes until the load cell was triggered. Triggering of the load cell indicated collapse of the respirator, and the test was ended. The flow rate at which the respirator collapsed was recorded as the measure of collapse resistance and recorded in 1/m.

Example 1

A respirator was constructed by the procedures detailed in the General Mask Making Procedure using a reinforcing weld pattern in the form of an isosceles triangle with two nested isosceles triangles located in corners opposite the equal-length sides of the larger triangle, as is generally depicted in FIGS. 2 and 3 as 32*a*, 32*b*, 32*c*, and 32*d*. Each smaller triangle shared an equal-length side and the remaining side with the larger triangle. The equal-length sides of the larger triangle were 52 mm with the equal-length sides of the nested triangles being 17 mm. The pattern was placed in four quadrants on the face of the respirator defined by a transversely-extending line of demarcation and a longitudinal axis. The transversely-extending line of demarcation was located 93.5 mm down from the top of the mask with the longitudinal axis located along the center-line of the mask. Quadrants 1, 2, 3, and 4 were defined by clockwise positions: 9:00 to 12:00, 12:00 to 3:00, 3:00 to 6:00, and 6:00 to 9:00 respectively. The geometric centroids of the large triangles were centered in each quadrant and placed 44 mm along radial lines from the point of intersection of the transversely-extending line of demarcation and a longitudinal axis. Large triangles in quadrants 1 and 2 had their apexes pointing towards the upper part of the mask and base parallel to the transversely-extending line of demarcation. Large triangles in quadrants 3 and 4 pointed towards the bottom of the mask but also with their base parallel to the transversely-extending line of demarcation. Welded width of the reinforcing patterns was 3 mm, and covered 651 square mm for each quadrant. Welds fused the preform through all layers.

Comparative Example 1

A mask was formed and tested as described in Example 1 except that no reinforcing pattern was used. Test results are given in Table 2.

Example 2

A mask was formed and tested as described in Example 1 except that a 34 gsm inner cover web and outer scrim of polypropylene spun-bonded nonwoven, available from Shandong Kangjie Nonwovens Co. Ltd., Jinan, China were used in the Preform Making Stage. Test results are given in Table 2.

Comparative Example 2

A mask was formed and tested as described in Comparative Example 1 except that a 34 gsm inner cover web and outer scrim were used in the Preform Making Stage. Test results are given in Table 2.

The masks were tested according to the Simulated Breathing Apparatus and Collapse Resistance Test protocol. Test results and testing parameters are given in Table 2:

TABLE 2

| Example | Weld Pattern | Outer Scrim/Inner Cover Web Weight (gsm) | Collapse Failure Point (l/min) |
|---|---|---|---|
| Example 1 | Nested triangle | 17 | 55 |
| Comparative Example 2 | None | 17 | 45 |
| Example 2 | Nested triangle | 34 | 95 |
| Comparative Example 2 | None | 34 | 100 |

The test results indicate that the collapse resistance of masks, formed with weld reinforcing patterns, had a greater effect on lighter-weight constructions than heavier constructions. The truss-type weld pattern provided improvement of collapse resistance for the lighter-weight mask construction relative to a mask of that construction with no weld pattern.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A flat-fold, filtering face-piece respirator that comprises:
(a) a mask body that has a transversely-extending line of demarcation, a longitudinal axis, first and second weld patterns disposed above and not traversing the line of demarcation on each side of the longitudinal axis, respectively, and third and fourth weld patterns disposed below and not crossing the line of demarcation on each side of the longitudinal axis, respectively, wherein each of the first, second, third, and fourth weld patterns is a two-dimensional enclosed pattern; and
(b) a harness secured to the mask body.

2. The flat-fold filtering face-piece respirator of claim 1, wherein each weld pattern has a truss-type geometry.

3. The flat-fold, filtering face-piece respirator of claim 1, wherein each weld pattern comprises one or more triangles.

4. The flat-fold filtering face-piece respirator of claim 3, wherein each of the triangles at each of the weld patterns comprises rounded corners.

5. The flat-fold filtering face-piece respirator of claim 4, wherein each of the weld patterns comprises a triangle nested within a triangle.

6. The flat-fold filtering face-piece respirator of claim 5, wherein the weld pattern comprises first and second triangles nested within a larger triangle.

7. The flat-fold filtering face-piece respirator of claim 6, wherein the first and second triangles are located at corners of the larger triangle and share weld lines therewith.

8. The flat-fold filtering face-piece respirator of claim 1, wherein each of the first, second, third, and fourth enclosed weld patterns occupies an area of about 5 to 30 $cm^2$.

9. The flat-fold filtering face-piece respirator of claim 1, wherein each of the first, second, third, and fourth enclosed weld patterns occupies an area of about 10 to 16 $cm^2$.

10. The flat-fold filtering face-piece respirator of claim 1, wherein each weld pattern comprises a quadrilateral.

11. The flat-fold filtering face-piece respirator of claim 1, wherein each weld line in each weld pattern comprises a single line that is about 2 to 7 mm thick.

12. The flat-fold filtering face-piece respirator of claim 1, wherein each weld line in each weld pattern comprises a single line that is about 4 to 5 mm thick.

13. The flat-fold filtering face-piece respirator of claim 1, wherein the mask body includes a top portion and a bottom portion, wherein the top portion and the bottom portion are separated by the line of demarcation.

14. The flat-fold filtering face-piece respirator of claim 13, wherein the line of demarcation is a pleat that extends transversely across a central portion of the mask body.

15. The flat-fold filtering face-piece respirator of claim 13, wherein the mask body comprises a plurality of pleats, at least one pleat being located above the line of demarcation and at least one pleat being located below the line of demarcation.

16. The flat-fold filtering face-piece respirator of claim 1, wherein the mask body comprises a filtering structure that includes a filtration layer and one or more cover web layers; the filtration layer and the one or more cover web layers being welded together at each of the first, second, third, and fourth weld patterns.

17. The flat-fold filtering face-piece respirator of claim 1, wherein the harness comprises one or more straps, and wherein the mask body comprises a filtering structure that comprises a layer of filter media and one or more cover webs, the filtration layer and the one or more cover webs being welded at each of the first, second, third, and fourth weld patterns.

* * * * *

UNITED STATES PATENT AND TRADEMARK OFFICE

CERTIFICATE OF CORRECTION

PATENT NO. : 8,640,704 B2
APPLICATION NO. : 12/562239
DATED : February 4, 2014
INVENTOR(S) : Scott Spoo It is certified that error appears in the above-identified patent and that said Letters Patent is hereby corrected as shown below:

In the Specification:

Column 2
Line 14, delete "forth" and insert -- fourth --, therefor.

In the Claims:

Column 14
Line 23, in Claim 1, before "third" delete "and".
Line 31, in Claim 3, delete "flat-fold," and insert -- flat-fold --, therefor.

Signed and Sealed this
Twenty-fourth Day of June, 2014

Michelle K. Lee
*Deputy Director of the United States Patent and Trademark Office*